United States Patent [19]

Wijngaarden et al.

[11] Patent Number: 5,175,374
[45] Date of Patent: Dec. 29, 1992

[54] PROCESS FOR THE SEPARATION OF COLLOIDAL BARIUM PHOSPHATE OR COLLOIDAL BARIUM SODIUM PHOSPHATE

[75] Inventors: Rudolf J. Wijngaarden; Kees Latjes; Jan Van Schaik, all of Amsterdam, Netherlands

[73] Assignee: Shell Oil Company, Houston, Tex.

[21] Appl. No.: 905,613

[22] Filed: Jun. 29, 1992

[30] Foreign Application Priority Data

Jul. 18, 1991 [GB] United Kingdom ............... 9115507

[51] Int. Cl.$^5$ .................................... L07L 41/40
[52] U.S. Cl. ...................................... 568/621; 568/45; 568/608; 554/149; 560/248; 564/497
[58] Field of Search .................. 568/621, 608, 45; 554/149; 560/248; 564/497

[56] References Cited

U.S. PATENT DOCUMENTS 4,967,016  10/1990  Kemp .

Primary Examiner—Howard T. Mars

[57] ABSTRACT

The invention relates to a process for the separation of colloidal barium phosphate or colloidal barium sodium phosphate, used as a heterogeneous catalyst in the alkoxylation of an active hydrogen containing organic compound, from the alkoxylated product, which process comprises contacting the alkoxylated product with an amount of water sufficient to break the colloidal state of the barium phosphate or barium sodium phosphate, and collecting the phosphate.

7 Claims, 1 Drawing Sheet

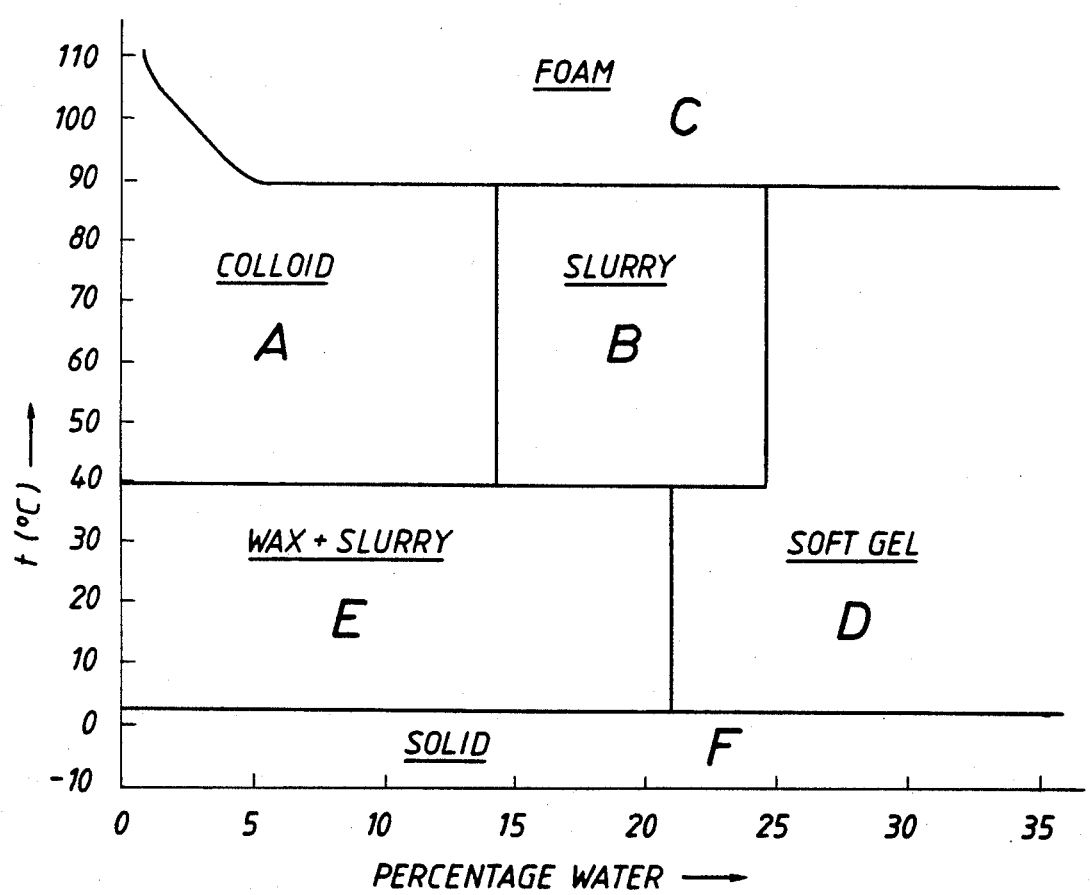

PROCESS FOR THE SEPARATION OF COLLOIDAL BARIUM PHOSPHATE OR COLLOIDAL BARIUM SODIUM PHOSPHATE

FIELD OF THE INVENTION

The invention relates to a process for the separation of colloidal barium phosphate or barium sodium phosphate, used as a heterogenous catalyst in the alkoxylation of an active hydrogen containing organic compound.

BACKGROUND OF THE INVENTION

From U.S. Pat. No. 4,967,016 it is known that alkylene oxides react with active hydrogen containing organic compounds, such as alcohols, phenols and polyols in the presence of a catalytically effective amount of barium phosphate. The separation of the barium phosphate still presents difficulties, because it is present in colloidal form in the reaction mixture. Removal of barium phosphate can only be carried out at a low temperature with a significant loss of alkoxylation product or with complicated working up procedures. The same applies for barium sodium phosphate, used as an alkoxylation catalyst.

A process has now been found in which these disadvantages are avoided.

SUMMARY OF THE INVENTION

The invention relates to a process for the separation of colloidal barium phosphate or colloidal barium sodium phosphate, used as a heterogenous catalyst in the alkoxylation of an active hydrogen containing organic compound, from the alkoxylated product which comprises contacting the alkoxylated product with an amount of water sufficient to break the colloidal state of the barium phosphate or barium sodium phosphate and collecting the phosphate.

BRIEF DESCRIPTION OF THE DRAWING

The FIGURE is a graph showing the various phases into which the colloidal barium phosphate or barium sodium phosphate is separated depending on the temperature and the amount of water used in the process.

DESCRIPTION OF THE PREFERRED EMBODIMENTS

The term "colloidal", as used herein, is applied to two-phase systems in which one of the phases is dispersed in the other in the form of finely divided particles. In the above case, the phosphate is dispersed in the reaction mixture in the form of finely divided particles. The particles have a size of less than 0.2 $\mu$m and they flow easily through filter paper.

Generally, colloids have the property that they flocculate out when subjected to an electrostatic field. They generally have the tendency to flocculate when acids, bases or salts are added to the two-phase system. In the process for the separation of barium phosphate or barium sodium phosphate, the amount of water to be added is preferably less than about 50 percent by weight basis on the weight of the alkoxylated product. The broken colloidal barium phosphate or barium sodium phosphate may be collected by filtration, centrifugation, decantation of the reaction product or other physical means. The barium phosphate and barium sodium phosphate, which were used as a heterogeneous catalyst in the alkoxylation reactions, are still present after the alkoxylation reaction and are chemically unchanged. Consequently, they may be reused after separation. The high temperature in the alkoxylation reaction have caused them to be in the form of colloids which must first be broken.

It is very surprising that the colloidal barium phosphate and barium sodium phosphate are broken by water. It has been found that under the conditions described according to the invention slurries of barium phosphate or barium sodium phosphate can be obtained, which can be easily worked up in an economical manner.

The invention preferably relates to a process for the separation of barium phosphate or barium sodium phosphate, used as a heterogenous catalyst in the alkoxylation of an active hydrogen containing organic compound, from the alkoxylated product, which process comprises adding to the alkoxylated product from about 15 percent by weight to about 35 percent by weight, calculated basis the weight of the alkoxylated product, of water, the temperature being in the range of from about 40° C. to about 95° C., and allowing the colloidal barium phosphate or barium sodium phosphate to break.

The reaction in which the barium phosphate or barium sodium phosphate has been used as heterogeneous catalyst, started with an alkylene oxide and an active hydrogen containing organic compound.

The alkylene oxides are particularly lower alkylene oxides, more particularly those in the range of from about 2 to about 4 carbon atoms. Preferred are ethylene oxide, propylene oxide or mixtures thereof, more preferred is ethylene oxide.

The active hydrogen containing organic compounds include alcohols, phenols, thiols (mercaptans), amines, polyols or carboxylic acids. A preferred group of compounds are the alcohols, specifically the primary monohydric alkanols, having carbon numbers in the range of from 6 to 24. The alkoxylation reactions and products (alkoxylated) have been described in U.S. Pat. No. 4,967,016, the teachings of which are incorporated herein by reference.

Acyclic aliphatic mon-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than 50 per cent, more preferably greater than 60 percent and most preferably greater than 70 percent of the molecules are of linear (straight-chain) carbon structure.

The general suitability of such alkanols as reactants in alkoxylation reactions is well recognized in the art. Commercially available mixtures of primary monohydric alkanols prepared via the oligomerization of ethylene and the hydroformylation or oxidation of hydrolysis of the resulting higher olefins are particularly preferred.

Overall, the two reactants are utilized in quantities which are predetermined to yield an alkoxylate product of the desired mean or average adduct number. Such products commonly have an average adduct number in the range from less than one to about 30 or greater, although the invention is also suitable for alkoxylation of reactants, such as polyols, for which substantially higher average adduct number products are often desired. In particularly preferred embodiments, the invention is applied for the manufacture of ethylene oxide adducts of primary mono-hydric alkanols in the carbon number range from about 6 to about 24, having an average of between 1 to about 15, more preferably between about 2 and about 12, oxyethylene groups per ethoxylate molecule, and characterized by very desirable adduct distribution.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature less than about 250° C., particularly less than about 210° C., and most particularly less than about 190° C., is typically desirable to minimize degradation of the product.

Superatmospheric pressures, e.g. pressures between about 0.7 and about 11 bars, are preferred, with pressure being sufficient to maintain the active hydrogen reactant substantially in the liquid state.

When the active hydrogen reactant is a liquid and the alkylene oxide reactant is a vapor, alkoxylation is the suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 4 bars, and/or the reactant is preferably diluted with an inert gas such as nitrogen, for instance, to a vapor phase concentration of 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between 3 and 7 bars, with an alkylene oxide partial pressure between 1 and 4 bars, is particularly preferred, while a total pressure of between 3.5 and 6.5 bars, with an alkylene oxide partial pressure between 1.5 and 3.5 bars, is considered more preferred.

Under the conditions of the alkoxylation reaction, the barium phosphate or the barium sodium phosphate are present at the end of the reaction in colloidal form in the alkoxylated product and breaking of the colloid is necessary separate the catalysts from the alkoxylated product.

In principle the obtained colloid of barium (sodium) phosphate is broken in a slurry, a foam, a soft gel or a wax plus slurry.

DETAILED DESCRIPTION OF THE DRAWING

In the FIGURE, on the vertical axis is the temperature given in degrees Celsius, and on the horizontal axis is the weight percentage of water, calculated basis the weight mixture of alkoxylated DOBANOL-1 (DOBANOL is a trademark of and sold by Shell Internationale Chemical Company) and water. In the FIGURE, several areas are depicted:

| | |
|---|---|
| colloid area | A |
| slurry area | B |
| foam area | C |
| soft gel area | D |
| wax/slurry area | E |
| solid area | F |

The colloid area A represents the are wherein the obtained hot alkoxylation reaction mixture is cooled to about 40° C. to about 95° C., and wherein a low water percentage does not break the colloid.

The slurry area B represents the are wherein the amount of water is sufficient to break the colloid into a slurry. The obtain particles have a diameter of 0.5-2 mm and can be separated by filtration or centrifugation.

The foam area C represents the area wherein the colloid is broken to a foam because of the high temperatures, generally above about 95° C.

The soft gel area D is the area wherein independent of the temperature by addition of much water a soft gel exists.

The wax/slurry area E is the area wherein at temperatures below about 40° C. wax and slurry area formed, whether a low percentage of water is added or a normal percentage.

The solid area F is present below about a few degrees Celsius.

In a preferred process for the separation of barium phosphate or barium sodium phosphate, the amount of water ranges from about 15 percent by weight to about 35 percent by weight, calculated basis the weight of the alkoxylated product; the temperature being in the range of from about 40° C. to about 95° C. This corresponds in the FIGURE with area B (the amount of water herein being based on the total amount of alkoxylated product and water).

It has been found that unless the amount of added water is small, the colloid is always broken. For the separation it is best that the slurry contains particles of about 0.5 to 2 mm, which latter can be collected by filtration or centrifugation.

The invention will now be further described by the following examples which are intended for illustrative purposes and are not to be construed as limiting the invention.

EXAMPLE 1

In a 5-liter autoclave were introduced 1000 g of DOBANOL-1 (a $C_{11}$-alcohol) and 15 g of barium phosphate. The mixture was kept under a nitrogen atmosphere of 2.5 bar (250 kPa) and stirred at 750 rpm, while the temperature in the autoclave was raised to 155° C. Ethylene oxide gas was then introduced into the autoclave, the total pressure being held at 4 bar (400 pKa). The ethylene oxide partial pressure was 1.5 bar (150 kPa), so that the gas cap contained always less than 40% ethylene oxide.

The alkoxylation reaction was continued with 1.8 kg of ethylene oxide was reacted with the alcohol, which was after 2 hours.

After the ethylene oxide gas stream was stopped, the autoclave was kept for an additional thirty minutes at 155° C. The alkoxylation reaction product was then cooled to 80° C. and kept under nitrogen atmosphere. It still contained the barium phosphate.

1000 Grams of the alkoxylated product/barium phosphate was admixed with 200 g of water of 80° C. The barium phosphate flocculated out within 5 minutes in 0.5–2 mm particles, which were partly removed from the alkoxylated product by filtration and partly by centrifugation at the temperature of 80° C. The alkoxylated product was dried and contained the narrow range ethoxylate $C_{11}H_{23}(OC_2H_4)_{6-7}OH$ with less than 1 ppm of barium phosphate. When alkoxylated product-/barium phosphate of 80° C. was not blended with water and directly filtered, the barium phosphate slipped through cotton filters of all pore diameters of 0.5 micron and higher. Even precoating the filters with Decalite or Celite did not prevent the barium phosphate colloid from running through the filter. This indicated that the colloid particles were less than 0.1 $\mu$m in diameter.

No substantial barium phosphate separation from the colloid could be achieved using centrifuges with centrifugal forces up to 12000 g.

The alkoxylated product/barium phosphate was brought in an electrical field (two 10 cm × 10 cm electrodes, potential difference 6000 V, positive electrode connected to earth) the barium phosphate flocculated on the negative electrode as coarse 0.5 to 2 mm particles.

From the above experiments it was concluded that the barium phosphate was present in the ethoxylate product as a colloid.

EXAMPLE 2

Similar to the process described in Example 1, 1000 g of DOBANOL-45 ($C_{14}$–$C_{15}$-alcohol) and 15 g of barium phosphate were charged to the reactor. 1.5 kg of ethylene oxide was reacted with the alcohol.

1000 G of ethoxylated product/barium phosphate of 80° C. was admixed with 200 g of water of 80° C. The barium phosphate flocculated out within 5 min and was removed by centrifugation or filtration.

EXAMPLE 3

Similar to the process described in Example 1, 1000 g of DOBANOL-91 ($C_9$ to $C_{11}$-alcohol) and 15 g of barium phosphate were charged to the reactor. 1.9 kg of ethylene oxide was reacted with the alcohol.

1000 Grams of ethoxylated DOBANOL-91/barium phosphate was admixed with 200 g of water of 80° C. The barium phosphate flocculated out within 5 min and was removed by centrifugation or filtration.

EXAMPLE 4

Similar to the process described in Example 1, barium sodium phosphate was used as a catalyst instead of barium phosphate.

1000 Grams of ethoxylated product/barium sodium phosphate of 80° C. was admixed with 200 g of water of 80° C. Also this colloid was broken and $BaNaPO_4$ flocculated out, when 20 g of water was 80° C. was added. It was removed by centrifugation or filtration.

EXAMPLE 5

Barium phosphate obtained after filtration in the process of Example 1 was charged to the reactor with 1000 g of fresh DOBANOL-1. The alcohol was reacted with ethylene oxide as described in Example 1. The recycled barium phosphate had the same activity as the fresh barium phosphate used in the process described in Example 1. The obtained alkoxylated product had the same properties as that in Example 1.

EXAMPLE 6

Hereinafter are described some working-up techniques with alkoxylated DOBANOL-1/barium phosphate blends, prepared according to the first part of Example 1:

| | |
|---|---|
| Cooling to 80° C., addition of water 10% | remained colloid. |
| Cooling to 80° C., addition of water 30% | colloid broken, soft gel. |
| Cooling to 40° C., addition of water 20% | colloid broken, could be filtered or centrifuged waxy. |
| Cooling to 100° C., addition of water 20% | colloid broken, difficult to be filtered or centrifuged because of foaming. |
| Cooling to 20° C., addition of water 20% | colloid broken, could be filtered or centrifuged, partly solid. |

What is claimed is:

1. A process for the separation of a colloidal barium phosphate or colloidal barium sodium phosphate, heterogeneous catalyst in the alkoxylation of an active hydrogen containing organic compound with an alkylene oxide reactant, from the alkoxylated product, which process comprises contacting at temperature in the range of from about 40° C. to about 95° C. the alkoxylated product with an amount of water sufficient to break the colloidal state of the barium phosphate or barium sodium phosphate, and collecting the phosphate.

2. The process as claimed in claim 1 wherein the amount of water is in the range of from about 15 percent by weight to about 35 percent by weight, basis the weight of the alkoxylated product.

3. The process as claimed in claim 1, wherein the broken colloidal barium phosphate or barium sodium phosphate is collected by filtration.

4. The process as claimed in claim 1, wherein the broken colloidal barium phosphate or barium sodium phosphate is collected by centrifugation.

5. The process as claimed in claim 1, wherein the alkoxylation reactant is selected from the group consisting of ethylene oxide and propylene oxide.

6. The process as claimed in claim 5, wherein the active hydrogen containing organic compound is selected from the group consisting of an alcohol, a phenol and a polyol.

7. The process as claimed in claim 6, wherein the alcohol is a primary mono-hydric alkanol having carbon numbers in the range of from about 6 to about 24.

* * * * *